(12) United States Patent
Sun et al.

(10) Patent No.: US 7,208,962 B2
(45) Date of Patent: Apr. 24, 2007

(54) DEVICE AND METHOD FOR DETECTING THE ENVIRONMENT CHANGE OF WINDSHIELD

(76) Inventors: Tengchen Sun, Room 351, No. 15 Building, Guanghuali, Chao yang District, Beijing City, P.R. (CN) 100020; Jie Yu, No. 3, Yannian Lane, Denei Street, Xicheng District Beijing City, P.R., Beijing (CN) 100009

( * ) Notice: Subject to any disclaimer, the term of this patent is extended or adjusted under 35 U.S.C. 154(b) by 0 days.

(21) Appl. No.: 10/595,085

(22) PCT Filed: Jun. 24, 2004

(86) PCT No.: PCT/CN2004/000682

§ 371 (c)(1),
(2), (4) Date: Feb. 3, 2006

(87) PCT Pub. No.: WO2005/029134

PCT Pub. Date: Mar. 31, 2005

(65) Prior Publication Data

US 2006/0290521 A1    Dec. 28, 2006

(30) Foreign Application Priority Data

Sep. 19, 2003  (CN) ................. 03 1 60008
Sep. 19, 2003  (CN) ................. 03 1 60009

(51) Int. Cl.
*G01R 27/26* (2006.01)
*G01N 5/02* (2006.01)

(52) U.S. Cl. ............................... 324/690; 73/73

(58) Field of Classification Search ........... 324/664, 324/665, 686, 689, 690
See application file for complete search history.

(56) References Cited

U.S. PATENT DOCUMENTS

| | | | |
|---|---|---|---|
| 3,826,979 A * | 7/1974 | Steinmann | 361/178 |
| 4,805,070 A | 2/1989 | Koontz et al. | |
| 5,668,478 A | 9/1997 | Buschur | |
| 5,880,538 A * | 3/1999 | Schulz | 307/109 |
| 2001/0030545 A1 | 10/2001 | Schmitt et al. | |

FOREIGN PATENT DOCUMENTS

| | | |
|---|---|---|
| CN | 88102294 A | 4/1988 |
| CN | 02147854 A | 5/2003 |
| DE | 3937605 A1 | 5/1991 |

(Continued)

OTHER PUBLICATIONS

English Translation of International Preliminary Report on Patentability for PCT/CN2004/000682, mailed Apr. 27, 2006.

(Continued)

*Primary Examiner*—Vincent Q. Nguyen
(74) *Attorney, Agent, or Firm*—Wood, Herron & Evans, LLP (57) ABSTRACT

A device and method for detecting environmental change of automobile windshield includes a plane capacitor having two electrodes disposed on a common plane on the inner surface of the windshield, and with a total area of said two electrodes less than 100 sq. centimeters. A sensor detection circuit is responsive to the change of capacitance of the plane capacitor to produce a control signal to control equipment work.

19 Claims, 9 Drawing Sheets

FOREIGN PATENT DOCUMENTS

| | | |
|---|---|---|
| EP | 0333564 A1 | 9/1989 |
| JP | 1983-58112852 A | 7/1983 |
| JP | 1985-60205247 A | 10/1985 |
| JP | 1987-62179651 A | 8/1987 |
| JP | 1997-9061394 A | 3/1997 |
| JP | 1997-9061547 A | 3/1997 |

OTHER PUBLICATIONS

International Search Report, PCT/CN2004/00682.

* cited by examiner

DEVICE AND METHOD FOR DETECTING THE ENVIRONMENT CHANGE OF WINDSHIELD

FIELD OF THE INVENTION

The present invention relates to a device for detecting environmental change of automobile windshield and a detecting method adopting this device.

BACKGROUND OF THE INVENTION

From the beginning of 21$^{st}$ century, automobile electronization and intelligentization have become the direction and front edge of the development of automobile industry technology, meanwhile the safety of automobile and driver-friendly features have also become a focus for many big automobile manufacturers. Automatic measurement system is not only a driver-friendly feature for drives, but also a major component of active safety system of automobiles. In rainy days or in environment with high humidity, heavy rainwater or fog on the surface of automobile windshield often affects the sight of drivers. However, existing technologies cannot provide an economical, practical, and mass market oriented method for sensing rain or fog on windshield automatically.

Traditionally, drivers would adjust the direction of automobile air outlet system manually, so that air could directly blow towards the windshield to disperse fog. However, frequently adjusting air outlet direction by hand will distract the driver and cause safety problems. Automatic demisting system has been put forward as a cutting-edge technology of electronic development of automobiles, which can automatically sense fogging degree on the inner surface of automobile windshield, and based on which, automatically adjust air outlet direction and volume of automobile air-conditioning system; and after the fog is blown away, it can automatically restore the air outlet direction and volume to its original state. To date, no application of automatic demisting system has been seen in automobile industry due to sensor issues, it is believed that automatic demisting system will gradually become a standard feature of automobiles in the near future. The key technology of automatic demisting system is fogging sensor technology, objectively speaking, up to now, no practical fogging sensor for automobiles has been found around the world.

Key technology of automatic wiper system in prior art is raindrop sensor technology, objectively speaking, up to now, raindrop sensor technology is still not mature enough around the world. Although some renowned automobile manufacturers, such as Volkswagen, Chrysler and Citroen have successfully equipped automatic wiper system on their cars, the immature raindrop sensor technology has brought a series of regrets including difficult installation, high cost and high mistaken action rate, etc.

Current raindrop sensor technologies can be divided into two types according to their installation forms, namely built-in type and built-out type; built-out type is to install a sensor on the outside of windshield, such as above engine hood, outside of automobile front, outer surface of automobile windshield, etc; the characteristic of built-out raindrop sensor is to directly contact and measure rainwater; as far as we know, built-out raindrop sensors can be divided into photoelectric type, conductive type, vibrating type and parallel-plate capacitor according to their work principle. Since most built-out raindrop sensors cannot be directly installed on outer surface of windshield within the scope where wiper can reach, they can only sense rainfall without sensing brushing effect of the wiper; consequently, only open-loop control system for wiper can be formed, and close-loop control system reflecting brushing effect of the wiper cannot be formed. In addition, built-out raindrop sensors have also such defects as easy to be polluted and damaged; hence, built-out raindrop sensor is seldom applied in automobile industry. Built-in raindrop sensor is usually installed on the inner surface of automobile windshield where the wiper can reach, which must adopt non-contact measurement technology, it has such advantages that it can sense the rainfall and brushing effect of the wiper simultaneous, so as to provide feedback signals for wiper control in time; it is installed inside of the vehicle which prevents being polluted or damaged from the environment. In modern automobile industry, built-in raindrop sensor has become the mainstream.

So far, most built-in raindrop sensors widely used in automobile industry are all photoelectric sensors. And the photoelectric sensors can be divided into two types; the first type is to install a camera on inner surface of automobile windshield, which utilizes imaging principle similar to camera to conduct image analysis and processing so as to sense variations of rainfall. The cost of apparatus, data processing circuit and computer for this kind of photoelectric sensor is very high, thus it has not been applied in automobile industry at present. So infra we only discuss the second type of photoelectric raindrop sensor which has been widely used in automobile industry. It is to install a pair of beam emitting and receiving devices on inner surface of automobile windshield, which utilize reflection and refraction of light, when raindrops are attached on outside surface of automobile windshield, the refractive index of light will change, thus resulting in change of receiving light intensity on the receiving end, then the raindrop sensor will transfer the change of light intensity into change of electric signals, and then sense the change of rainfall. Built-in photoelectric raindrop sensor has the following defects:

Small measurement area. When there is a light rain, the distribution of raindrops per unit area is not even, as a result, if the measurement area is small, the automatic wiper system will react slowly. In most cases, the emitter of photoelectric raindrop sensor is a point source of light, though lens or prism can be used to scatter the beam to a certain extent to expand refraction area, this will bring negative influence to the sensitivity of receiver component. Consequently, practical measurement area of photoelectric raindrop sensor is usually within 1–2 sq. centimeters; of course, more pairs of emitting and receiving ends can be used to enlarge measurement area, but this will greatly increase the cost.

Unable to measure thickness of rainwater adhered to windshield surface. When there is a heavy rain, outer surface of automobile windshield will be evenly covered by rainwater, in this case, the rainfall can only be measured by variations of thickness of rainwater adhered to the windshield surface, if it cannot measure the thickness variations of rainwater, the automatic wiper system will work slowly and then affect brushing effects. The working principle of photoelectric raindrop sensor is to use variations in refractive index of beams, however refractive index is only related to physical characteristics of the incidence plane, and it is irrespective of thickness of the substance. Therefore, photoelectric raindrop sensor cannot reflect variations in the thickness of rainwater.

Be vulnerable to interference of pollutants. When the outer surface of automobile windshield is polluted by pollutants (such as: dust, mud, stain and bodies of dead insects), the refractive index of beams will also change a lot, the automatic wiper will be caused undesired actions due to the fact that the photoelectric raindrop sensor cannot distinguish pollutants from rainwater.

High technical requirements for installation. Photoelectric raindrop sensor requires that the emitting and receiving end should have accurate installation angles and distances; meanwhile, it also has high requirements for both location and angle of the assistant lens and prism system; furthermore, considering influence of automobile vibration, the installation must be tight and stable to prevent the accuracy and sensitivity of the sensor from being affected by deviation of the beams which caused by automobile vibrating.

Bad adaptability. The working principle of photoelectric raindrop sensor has a bad adaptability to different automobile windshields, materials of the windshield will influence refractive index and reflectivity, thickness of the windshield will influence installation angle and location of both emitting end and receiving end, so different photoelectric raindrop sensors must be designed for different automobile windshields.

High cost of material, installation and man-hour. The cost of materials of photoelectric emitting and receiving device, lens and prism system and fasteners which photoelectric raindrop sensor required are higher, installation and man-hour cost are also very high due to high requirements for installation techniques, these are the fundamental reasons why automatic wiper system only appeared in medium and high class vehicles at present time.

In addition to the photoelectric raindrop sensor which is mentioned above, there are also a few capacitance raindrop sensors are used in prior art. For instance:

Chinese patent number: 02147854.6, this patent provides a built-out parallel-plate capacitance rainwater sensor formed by a parallel connection of several pieces of capacitance plates, the outer shell of the sensor has an inlet and outlet, which conducts direct-contact measurement of rainwater. This sensor has typical demerits of built-out rainwater sensor, i.e. it cannot reflect brushing effect of the wiper and cannot form close-loop control system; it is vulnerable to be polluted and damaged and has a complicated structure. This sensor adopts a traditional parallel-plate capacitance measurement principle.

Patent document U.S. Pat. No. 4,805,070A, the name of which is "capacitance coupled humidity sensor", its sense element is resistance network; it utilizes the parallel-plate capacitance principle to send variations of the resistance to signal generator and receiver by two unchangeable parallel-plate capacitance couplings. The essential of this sensor is traditional resistor-based humidity sensor; this technical solution only provides a non-contact connection method between the signal processing circuit and the sense element (resistor network) to avoid the problem of crossing the windshield to connect the leads. In the technical solution of above mentioned patent, the sense element is installed on outer surface of automobile windshield, which conducts direct contact measurement of rainwater, and when the sense element is installed on outer surface of automobile windshield, it has strict requirements for both materials and installation technology. For instance: it must be erosion-resisting, rub-proof, and pollution-preventing and should not influence normal actions of the wiper, etc. Meanwhile, the problem of electric connection of sense element must be resolved if performing contact measurement by installing sense element on outer surface of automobile windshield, so the technical solution of above-mentioned patent provides a very complicated non-contact connection method which forming a parallel-plate coupling capacitor between the crack of two layers of glasses and outer surface of automobile windshield, and the installation cost of this method must be high due to its over complicated technology.

The measurement principle of the technical solution provided by U.S. Pat. No. 5,668,478A is very similar to the technical solution provided by U.S. Pat. No. 4,805,070A, which is also a contact way to measure the variations of resistance and perform signal coupling by parallel-plate capacitance, it has the same defects as U.S. Pat. No. 4,805,070A.

Patent Document EP0333564A1, The electric rainwater detection device provided by this patent has utilized the principle of capacitance measurement, but the sensor provided by this patent is a typical built-out contact rainwater measurement sensor which requires an isolated cover layer with good water-proof performance. This sensor has typical defects of built-out rainwater sensor, which cannot reflect brushing effect of the wiper, and is incapable of forming close-loop control system; besides, it is vulnerable to be polluted and damaged with complicated structure.

Patent document DE3937605A1, The measurement principle of this sensor is the principle of traditional parallel-plate capacitance measurement, the technical solution of this patent published is the capacitive plate and the water layer can form a capacitor independently when a water layer emerges on the windshield. Obviously, this can only constitute two independent parallel-plate capacitors. The primary defect of said sensor is that it requires the capacitor plate must be installed between the two layers of glasses and the two functional films, which will no doubt limits applicable scope of this sensor, Because the windshields applied in automobile industry is available in both double layers and single layer at present. Besides, this sensor also has defects such as complicated structure, difficult installation, and trouble of wiring, etc.

SUMMARY OF THE INVENTION

One object of present invention is to overcome the above mentioned deficiencies of a great deal of prior art, and provide a device for detecting environmental change of rainwater/fog on automobile windshield surface, the structure of said device is simple, and it can overcome various defects including small measurement area, inability of measuring rainwater thickness, vulnerable to be disturb by pollutants, high installation requirements, low adaptability and high cost which exist in current photoelectric type of sense devices and plane capacitance type of sense devices.

Another object of present invention is to provide a method for detecting environmental changes of automobile windshield accurately, this method is simple, practical and easy to promote.

The device for detecting environmental change of automobile windshield according to the first object of present invention, a plane capacitor is disposed on the inner surface of the windshield, two electrodes of said plane capacitor are disposed on the same plane, the total area of said two electrodes is less than 100 sq. Centimeters, said plane capacitor is a sense element which detects the environmental change of the windshield surface and the environmental change after operating, said plane capacitor is electrically connected with a sensor detection circuit, the signal of capacitance changing which is affected by the outer environmental is transmitted to said sensor detection circuit, and said sensor detection circuit is responsive to the change of capacitance to produce a control signal to control the equipment work.

The method for detecting environmental change of automobile windshield according to the second object of present invention includes the following steps:

Initialize detecting device;

The signal generator of the detecting device generates a testing signal and said testing signal is transmitted to the plane capacitor;

Measure value variations of said testing signal;

Transmit said testing signal to the processing unit;

The processing unit generates a control signal according to variations of the testing signal;

Transmit control signals to the equipment;

The detecting device re-detects the windshield surface, generates feedback signals and transmits said signals to the processing unit, thus forms a close-loop control system.

Compared with prior art, the following advantages can be seen in the device for detecting environmental change of automobile windshield provided by present invention: the plane capacitor provided by present invention has broken the thinking set of the traditional parallel-plate capacitor sensor, the two electrodes of capacitor are not placed in a parallel way, instead, they are placed on the same plane to form a built-in plane capacitor sensor with the following advantages:

Large measurement area: the electrodes of plane capacitor can be made into any shapes, and the measurement area can be enlarged at discretion as long as it wills not influence sight of the driver, which can eliminate the defects of slow reflection in the measurement system brought by over small measurement area of photoelectric raindrop sensor.

Be able to measure thickness of rainwater adhered to the windshield surface. As the medium space of the plane capacitor is a space approximately like half-elliptic sphere around the windshield above the electrodes, the windshield surface and vicinity of outer surface, within the scope of this space, variations in thickness of rainwater will lead to variations of dielectric constant of the capacitor medium space, thus causing variations in capacitance. This could overcome the defects of influencing rain-brushing effect due to slow speed in actions of the automatic wiper system brought by photoelectric raindrop sensor cannot detect variations in thickness of rainwater.

Not susceptible to be disturbed by pollutants. As relative dielectric constant of water is much higher than general pollutants, the plane capacitor sensor is easy to distinguish the variations of capacitance caused by pollutants and water, thereby solving the problem of error actions in automatic wiper system caused by the fact that the photoelectric raindrop sensor is influenced by pollutants.

Simple installation process. Plane capacitor sensor can form a plane capacitor on the inner surface of the windshield by adopting bonding, compression joint, spraying or various technologies of plating metal on a windshield surface, it does not need to accurately locate the place like photoelectric raindrop sensor.

Strong adaptability: As dielectric constant of water is several decades times larger than the glass, the influence caused by variations of glass materials and thickness to accuracy and sensitivity of sensor can be neglected. A same plane capacitor sensor can almost suit to all automobile windshields, and there is no need to design specific sensor for various automobile windshields.

Obvious decrease in cost of materials, installation and man-hour. Plane capacitor sensor can use many kinds of conductive materials, such as: copper foil, aluminium foil, conductive rubber, conductive plastic film, sprayed or plated metals on glass surface, etc.; meanwhile only little amount is required, generally speaking, only about 10 sq. centimeters is required, hence, the material cost is extremely low. The cost of installation and installation man-hour are also much lower than that of photoelectric raindrop sensor due to its simple installation.

The present invention can measure fog in a car, thus the problem of no applicable fogging sensor in the automatic demisting system of automobile windshield is solved. The plane capacitor sensor provided by present invention can effectively sense fogging degree within the inner surface of automobile windshield, and directly transmit digital signals to the automatic demisting system of automobile glass, subsequently on the basis of these signals, the automatic demisting system of automobile windshield can automatically adjust air outlet direction and air volume.

The method for detecting environmental change of automobile windshield according to present invention has the following advantages: Be able to process all testing signals in time; control operation of related equipments and realize rain-removal and demisting of windshield, this method is easy to realize and is suitable for promotion and application.

The present invention will be described in detail in combination with the embodiments given by the attached figures.

DETAILED DESCRIPTION OF PREFERRED EMBODIMENTS

Before explaining this invention in detail, there is a brief description of the working principle of present invention and the prior art:

Traditional capacitor sensor is based on parallel plate capacitor, the principle of which is: if the edge effect of non-uniform electric field is not considered, the capacitance of a capacitor composed of two parallel plates is $C=\in \cdot S/d$.

In this formula, $\in$ stands for dielectric constant of the medium between electrodes, $\in = \in 0 \cdot \in r$, $\in 0$ stands for dielectric constant of vacuum, $\in 0 = 8.854 \cdot 10^{-12}$ F/m, $\in r$ stands for dielectric constant of the medium relatives to vacuum, the relative dielectric constant of air is $\in r \approx 1$, other mediums: $\in r > 1$; S stands for area of the electrodes, and d stands for distance between the electrodes.

As the changing of the medium being measured could lead to variations of relevant parameters of $\in$, S, d of capacitor sensor and then make capacitance C changing accordingly. According to this, traditional capacitor sensors can be classified into three categories according to variations of different parameters: variable distance (parameter d change); variable area (parameter S change); variable dielectric constant (parameter $\in$ change).

The plane capacitor according to present invention has, from a point view of principle, broken the traditional thinking set of capacitor sensor based on parallel plate capacitance principle. It puts two electrodes of a capacitor on a same plane according to a certain distance instead of placing them in a parallel way. It does not belong to any type of said three traditional capacitor sensors; it is a comprehensive capacitor sensor combining features of variable distance, variable area and variable dielectric capacitance sensor.

Figure 1:
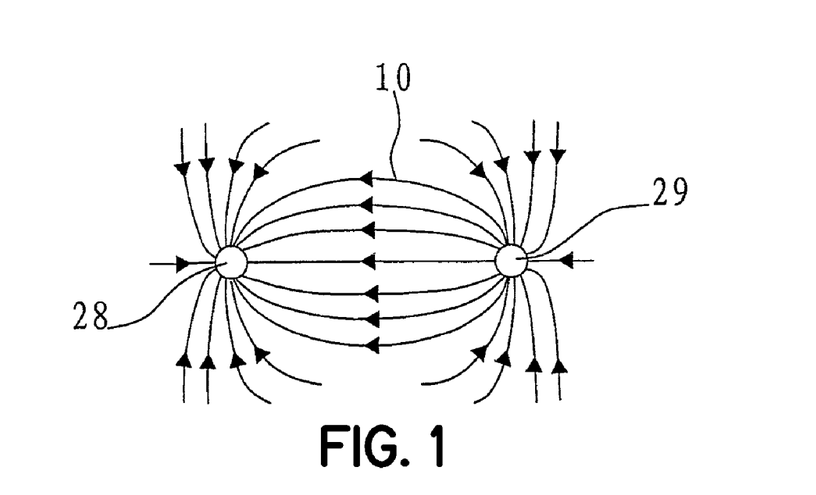
FIG. 1 is a distribution diagram of electric field line of point charge.
Figure 2:
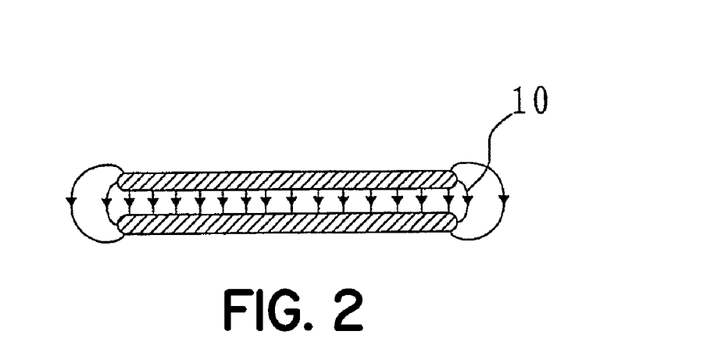
FIG. 2 is a distribution diagram of electric field line of parallel-plate capacitance.
Figure 3:
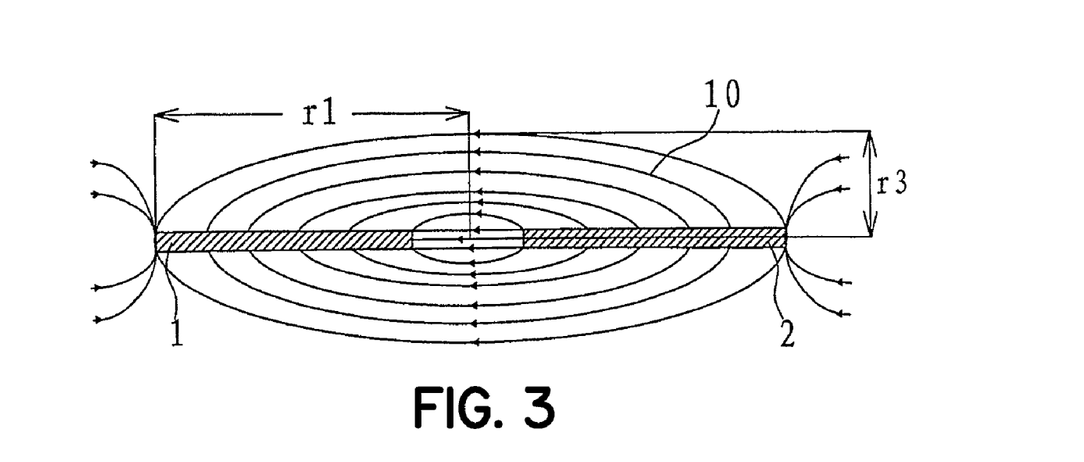
FIG. 3 is a distribution diagram of electric field line of a plane capacitor composed of 2 pieces of fan-shaped electrodes.
Figure 4:
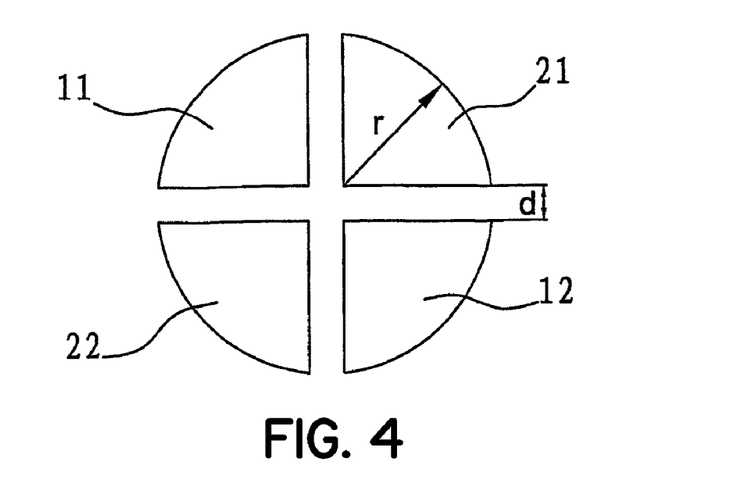
FIG. 4 is a schematic diagram of a plane capacitor composed of 4 pieces of fan-shaped electrodes according to one embodiment of present invention.

The capacitance measurement principle of present invention is as follows:

According to the principle of superposition field strength vector, we know that the features of capacitor can be described by the distribution of electric field line, referring to FIG. 1 and FIG. 2, which show the distribution of electric field line of point charge and parallel-plate capacitance respectively. In the FIGS. 10 is electric field line; 28 and 29 are point charge. To facilitate the following discussion, FIG. 3 provides an electric field distribution of a semicircle plane capacitor. From FIG. 2 we can see that the electric field line 10 of parallel-plate capacitor is mainly distributed among the rectangular space between the two parallel plates, so we can neglect the influence of the edge electric field of the parallel plates when calculating capacitance of the parallel-plate capacitor and conclude a formula for computing capacitance of the parallel-plate capacitor: $C=\in \cdot S/d$. For the same principle, we can see from FIG. 3 that electric field of plane capacitor mainly distributes in a space approximately like elliptic sphere around the two planar electrodes, as the theoretical calculation of plane capacitance is very complicated, we will not discuss it in detail here. Referring to FIGS. 3 and 4, it can be concluded from the principle of superposition vector as well as the characteristics of electric medium when it is in electric field that the radius of horizontal long axis in the magnetic field approximately like elliptic sphere around the two planar electrodes $r1 \approx r+d/2$, while the radius of horizontal short axis $r2 \approx r$, the radius of vertical short axis r3 can be approximately regarded as in direct ration with r and d respectively and in inverse ration with dielectric constant of medium.

Figure 5:
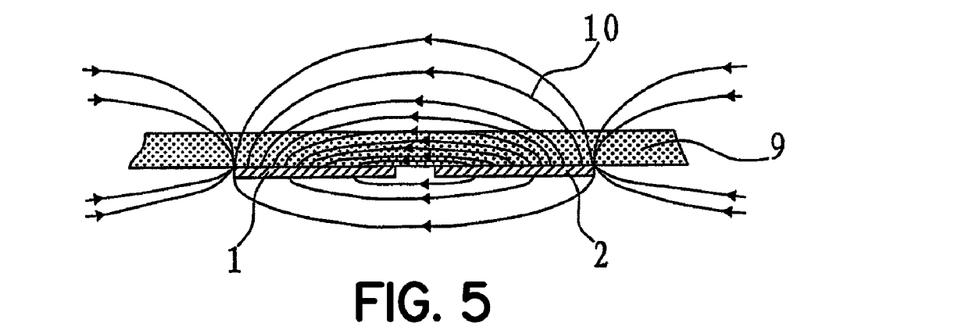
FIG. 5 is a distribution diagram of electric field line of a plane capacitor composed of 2 pieces of fan-shaped electrodes involved in medium environment of present invention.
Figure 6:
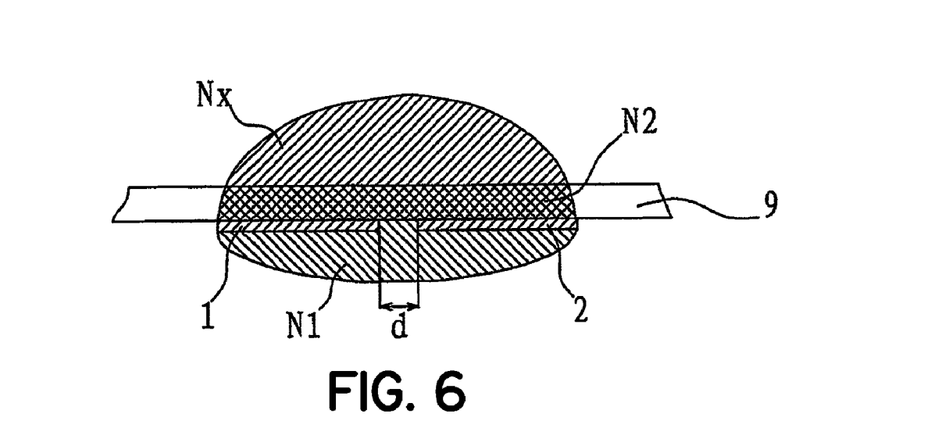
FIG. 6 is a schematic diagram of measurement space formed by a plane capacitor composed of 2 pieces of fan-shaped electrodes involved in medium environment of present invention.

Referring to FIGS. 5 and 6, which illustrate electric field space distribution of plane capacitor under application environment involved in present invention, the two planar electrodes 1 and 2 are closely clinging to the bottom of glass 9, We can see from the distribution shapes of electric field line 10 in FIGS. 5 and 6 that due to different medium impacts, the space approximately like elliptic sphere around the two planar electrodes 1 and 2 can be divided into three different spaces: N1—a space approximately like half-elliptic sphere under the inner surface of automobile windshield 9 as well as planar electrodes 1 and 2 that are closely sticking to the inner surface; N2—a flat elliptic space above planar electrode 1 and 2 as well as those contained in the inside of automobile windshield 9; Nx—a half-elliptic space formed around outer surface of automobile windshield 9. As the medium of N1—a space approximately like half-elliptic sphere and N2—a flat elliptic space is even air and glass respectively, their dielectric constant and volume can be regarded as changeless. And the medium of Nx—a half-elliptic space is usually air, when a foreign body enters, its dielectric constant and volume will change significantly, the half-elliptic space Nx is just our measurement space.

Figure 7:
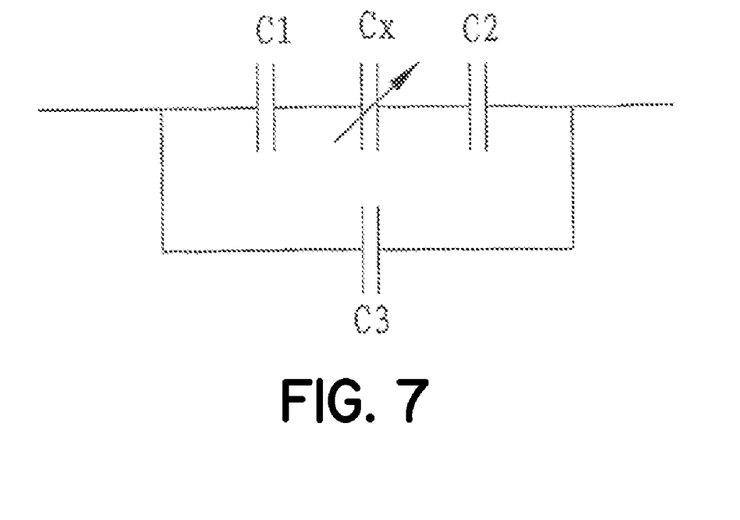
FIG. 7 is a model diagram of equivalent capacitance measurement of present invention.

Based on the above mentioned discussion, please refer to FIG. 7 for the equivalent capacitance model proposed by present invention. Among which, The parallel equivalent capacitance C3 is a invariable capacitance set by N1—a space approximately like half-elliptic sphere and N2—a flat elliptic space, series-wound capacitance C1 and C2 are invariable capacitance defined by the space above the planar electrode which passes through outer surface of automobile windshield but within the closure of outer surface of automobile windshield, Cx is a variable capacitance formed by half-elliptic space Nx. The capacitance of Cx is simultaneously decided by dielectric constant and covering area of the foreign body entering into the half-elliptic space Nx as well as the thickness the foreign body forms in the half-elliptic space Nx, this thickness can be, theoretically, equal to the spacing of the parallel plate capacitor.

We can get the following two conclusions from the above mentioned discussion concerning the principle of present invention:

The planar capacitor provided by present invention is different from any kind of former capacitor sensors including: variable area, variable distance and variable dielectric constant type, it is a comprehensive capacitor sensor which can sense variations of three parameters consisting of area, distance and dielectric constant at the same time.

The planar capacitor provided by present invention can differentiate foreign bodies around automobile windshield surface and simultaneously sense the area and thickness covered by foreign bodies on the automobile windshield surface of the sensor, which cannot be done by current photoelectric sensor.

After explaining the principle of present invention, now we describe the device for detecting environmental change of automobile windshield produced by utilizing the above mentioned principle, the environmental change mentioned here is mainly directed to rainwater on the outer surface of automobile windshield and fog on the inner surface of the windshield, the principle and equipment used by the two items are basically same, the only difference is the shapes of plane capacitor. Thus, we will first explain present invention in respect of technical solution for sensing rainwater of outer surface of windshield and automatically control the wiper.

Figure 9:
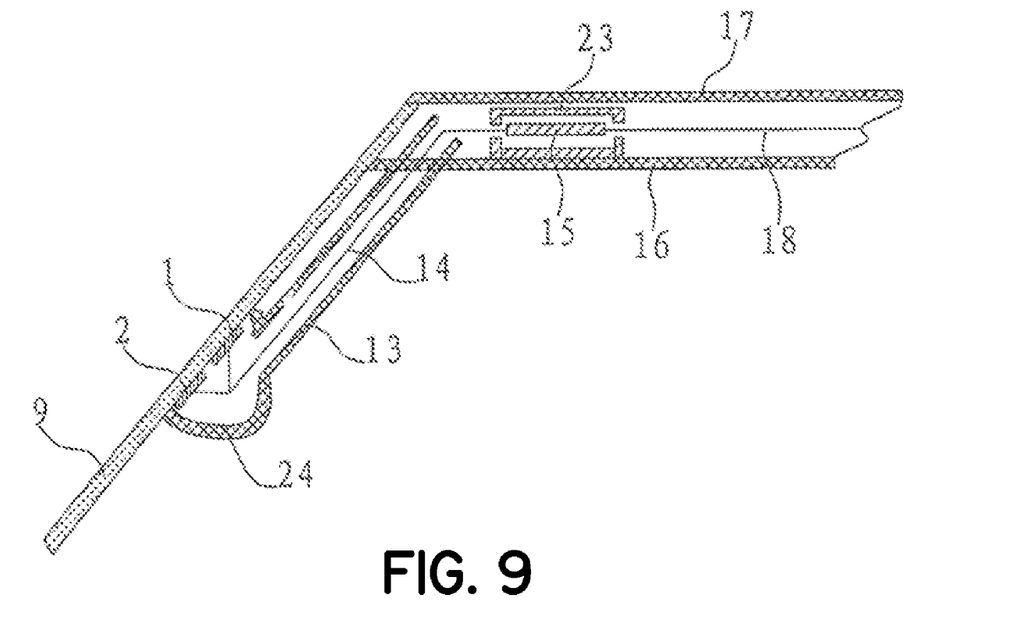
FIG. 9 is an installation structure section diagram of one embodiment of present invention.
Figure 10:
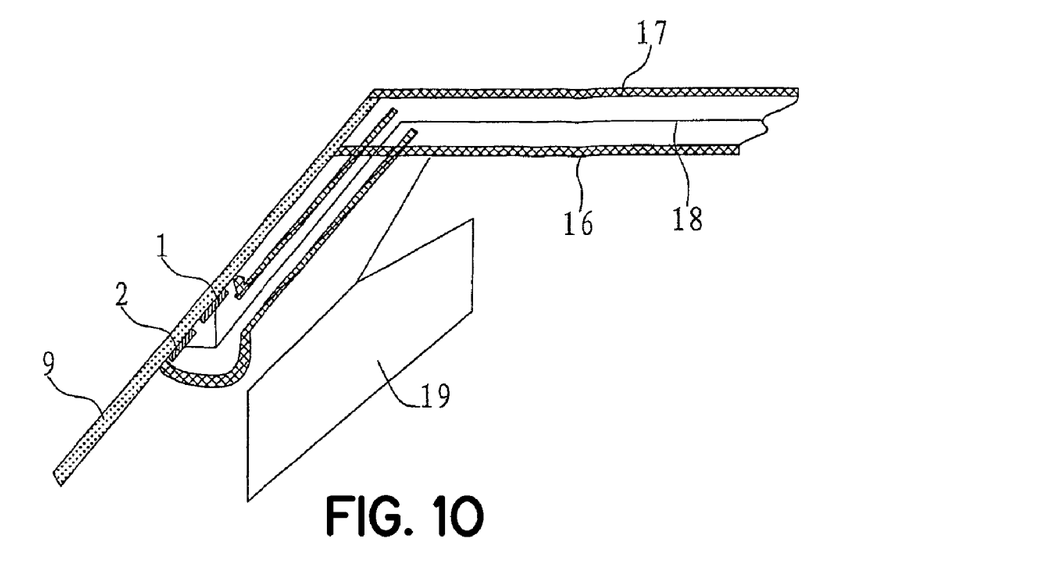
FIG. 10 is a schematic diagram of installation location of one embodiment of present invention.

Referring to FIGS. 4, 9 and 10, as a preferred embodiment of automatic wiper sensor, a copper foil with self adhesive tape on one side is made to 4 pieces of fan-shaped electrodes 11, 12, 21 and 22 with a radius of r=2 cm, the total area of above mentioned electrodes 11, 12, 21 and 22 is about 12 cm$^2$, said electrodes 11, 12, 21 and 22 are adhered to the inner surface of automobile front windshield 9 and behind of the automobile rear view mirror 19 without influencing sight of the driver, so two electrodes of the plane capacitor are formed. A non-contact measurement objective can be realized by installing them on the inner surface of the automobile windshield 9. Meanwhile, the installation position of said plane capacitor should belong to work range of rain-brushing of the wiper, which will not only measure whether rain exists on the windshield surface or not, but also measure the work effect of the wiper. The distance between the electrodes 1 and 2 is d=4 mm. One end of two shielded wires 14 are soldered on two electrodes 1 and 2 of the plane capacitor respectively; to prevent accidental damages, a conical plastic protective cap 24 is covered on back of the planar electrodes 1 and 2, the conical plastic protective cap 24 is adhered to the inner surface of automobile front windshield 9; to safeguard shielded wires 14, introduce shielded wires 14 through plastic sleeve 13 placed on side of the conical plastic protective cap 24 to the interlayer between outer shell of roof 17 and inner decoration of roof 16, the two shielded wires 14 are electrically connected on circuit board 15 which is located in said interlayer between outer shell of roof 17 and inner decoration of roof 16, said circuit board 15 will be electromagnetically shielded and protected by a shielded plastic outer shell 23, digital output signals of the sensor will be transmitted to control units of the automatic wiper system through shielded LIN cable 18.

Figure 8:
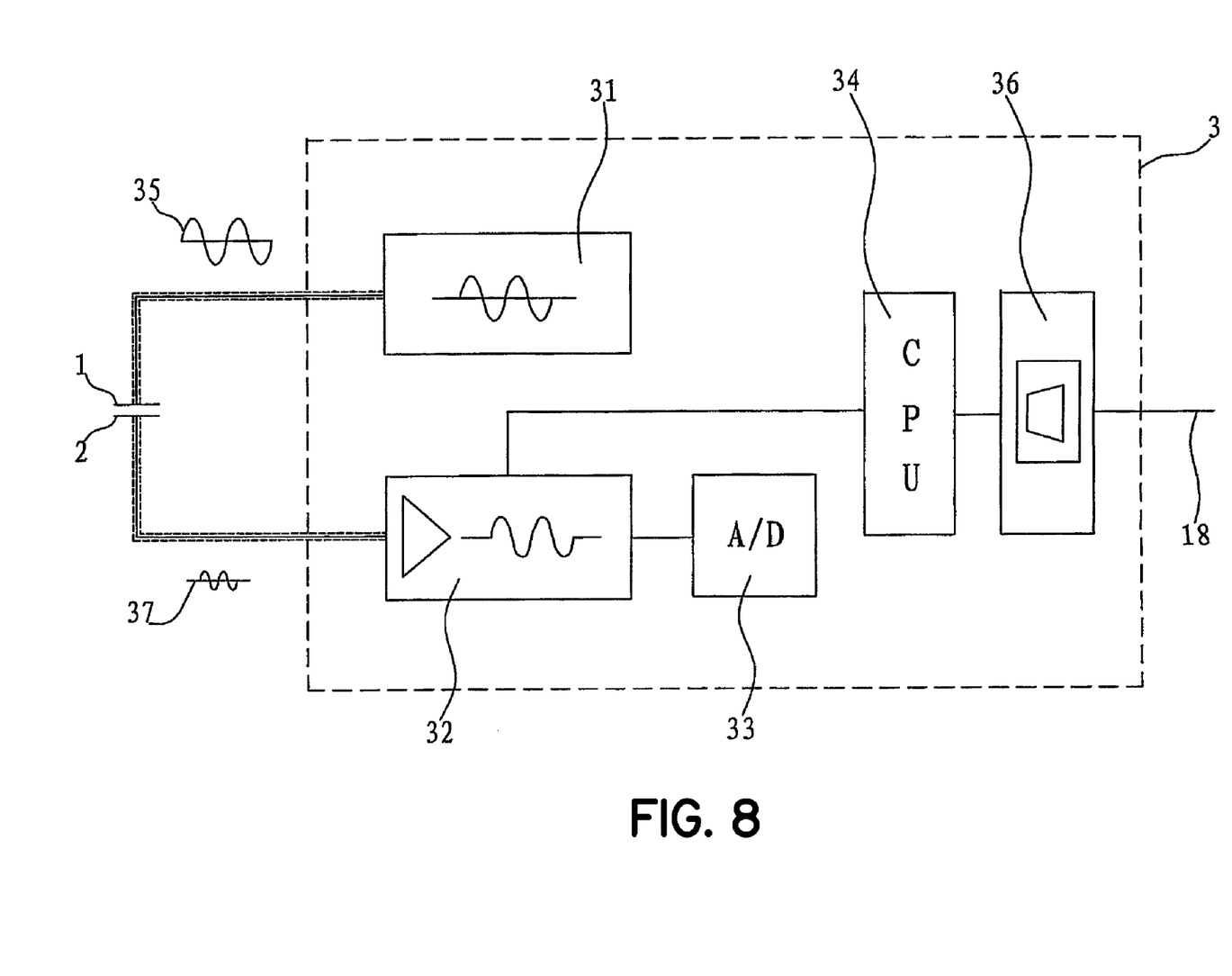
FIG. 8 is a testing circuit diagram of present invention.

Referring to FIG. 8, in the above mentioned embodiment of present invention, one electrode of the plane capacitor is connected with output end of the sine-wave signal generator 31; the other electrode of the plane capacitor is connected with input end of programme-controlled analog signal magnifier and filter circuit 32, the latter accepts programme control from micro processor 34 to conduct range self-adaptive adjustment, a sine-wave signal 35 generated by sine-wave signal generator 31 with a certain frequency will be reduced to sine-wave signal 37 after passing through plane capacitor, the signal 37 will be accepted by programme-controlled analog signal magnifier and filter circuit 32, and generate a DC voltage signal after being magnified and filtered, which will be converted to digital voltage signals via analog-to-digital conversion circuit 33 and be sent to micro-processor 34, the digital voltage signal will, after being digital filtered, digital linearized processed and digital self-adaptive arithmetic adjusted in micro processor 34, form digital output signals of the sensor and be delivered to bus line interface circuit 36 of shielded LIN (Lcal Interconnect Network) then, be delivered to control units of automatic wiper system through shielded LIN bus line cable 18. When the wiper starts to work, this device continues to detect the surface of windshield and generate feedback signals to further control the wiper to work and for a close-loop control system, so as to enable the device to control the wiper working according to sizes of raindrops. The testing signal of the present invention can also be square wave signal and triangle wave signal.

Figure 11:
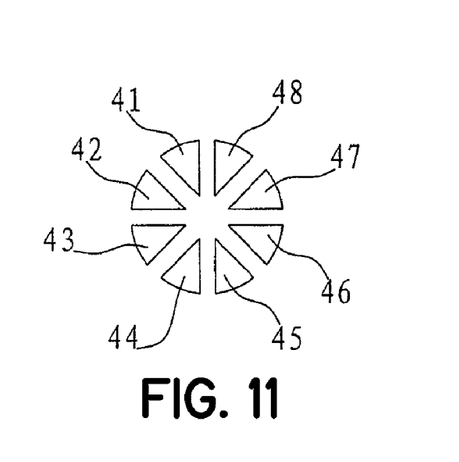
FIG. 11 is a schematic diagram of a plane capacitor composed of 8 pieces of fan-shaped electrodes of present invention.
Figure 12:
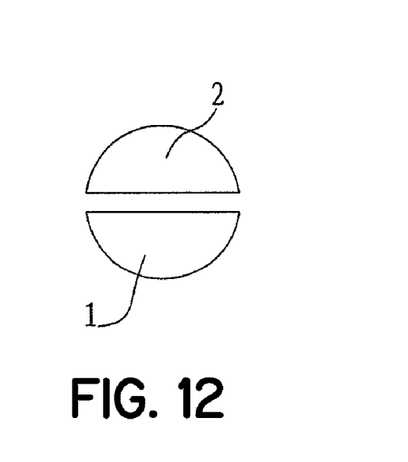
FIG. 12 is a schematic diagram of a plane capacitor composed of 2 pieces of fan-shaped electrodes of present invention.
Figure 13A:
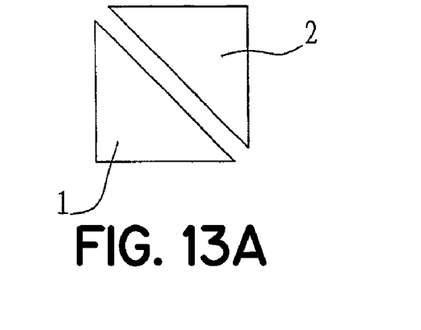
FIG. 13A is a schematic diagram of a plane capacitor composed of 2 pieces of triangle electrodes of present invention.
Figure 13B:
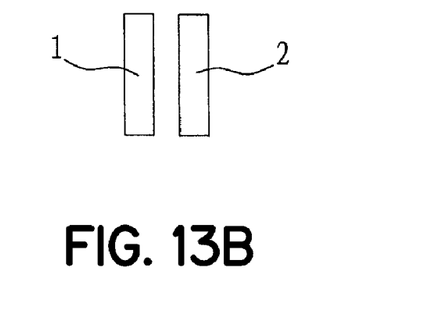
FIG. 13B is a schematic diagram of a plane capacitor composed of 2 pieces of rectangle electrodes of present invention.
Figure 14:
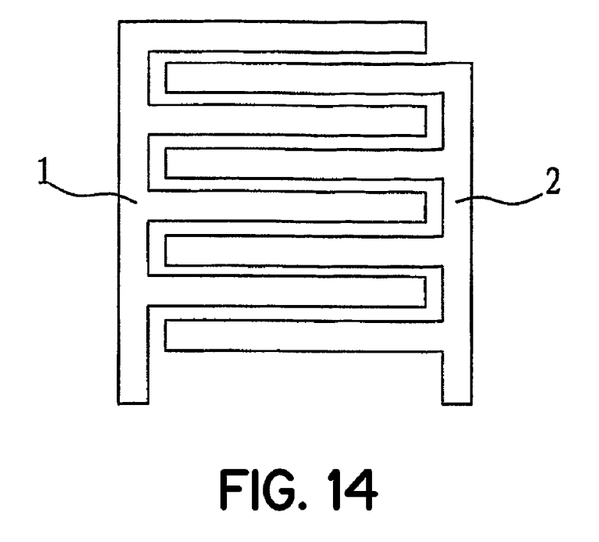
FIG. 14 is a schematic diagram of a pectinate plane capacitor of present invention.

Referring to FIG. 4, 11 to 14, in the above mentioned embodiment of present invention, the conductive materials used for the electrodes of said plane capacitor could be copper, aluminium, silver, conductive rubber, conductive plastics, conductive glue and transparent conductive film which are installed by various means, such as: bonding, compression jointing and spraying, thereby forming a pair of planar electrodes on a position of automobile windshield surface not influencing sight of the driver; the planar electrode can be in various shapes, including rectangle, fan, triangle and polygon, such as the plane capacitor composed of 4 pieces of fan-shaped electrodes shown in FIG. 4, the plane capacitor composed of 8 pieces of fan-shaped electrodes shown in FIG. 11, the plane capacitor composed of 2 pieces of fan-shaped electrodes shown in FIG. 12, the plane capacitor composed of 2 pieces of triangle electrodes shown in FIG. 13A, the plane capacitor composed of 2 pieces of rectangular electrodes shown in FIG. 13B and the plane capacitor composed of pectinate electrodes shown in FIG. 14. When there are several pieces of electrodes, use leads to connect them respectively to form two electrodes of a plane capacitor; in the plane capacitor composed of 4 pieces of fan-shaped plates shown in FIG. 4, plate 11 and plate 12 are connected to form one electrode of the plane capacitor, and plate 21 and plate 22 are connected to form another electrode of the plane capacitor; in the plane capacitor composed of 8 pieces of fan-shaped plates shown in FIG. 11, plates 41, 43, 45 and 47 are connected to form one electrode of the plane capacitor, and plates 42, 44, 46 and 48 are connected to form another electrode of the plane capacitor. When installing, it must be guaranteed that the electrodes of the plane capacitor must be in close contact with the inner surface of glass to avoid influencing performance of the sensor by air space, and the best choice is to plate metal on the glass surface. Experiments show that total area of the electrode less than 100 cm$^2$ will be acceptable, however, considering of cost saving and using effect, 10–20 cm$^2$ is preferred. The distance d between the two electrodes should be almost equal to the thickness of the automobile windshield. Static capacitance value of the plane capacitor should be between 0.2–5 pf, and the measurement sensitivity of the capacitance value should be higher than 0.1 pf.

After explaining the technical solution of detecting rainwater of outer surface of windshield and automatically controlling the wiper in present invention; the below is the explanation of the technical solution applied in the invention in detecting fogging degree of the inner surface of automobile windshield.

Figure 15:
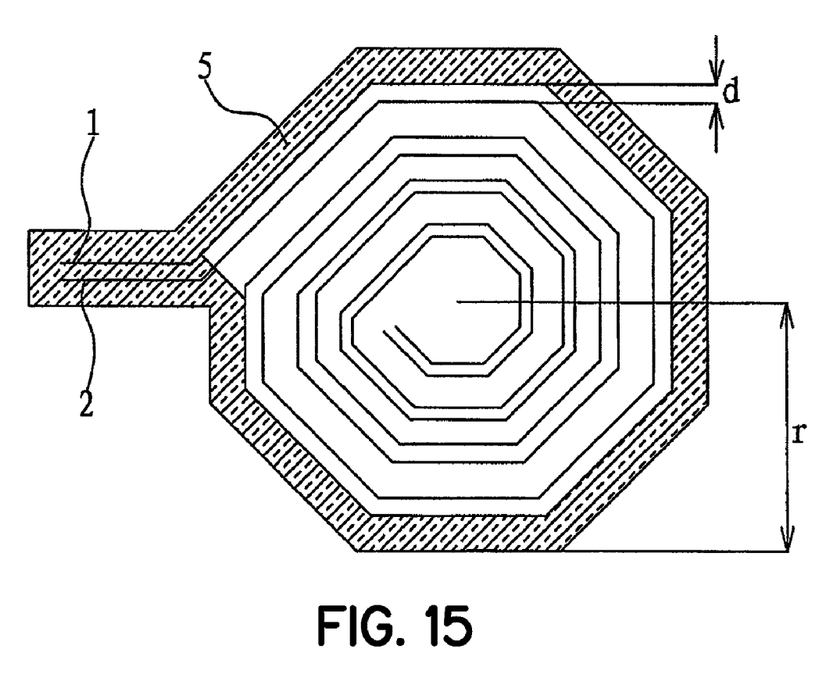
FIG. 15 is a schematic diagram of a plane capacitor of another embodiment of present invention; the plane capacitor is composed of planar curve electrodes.
Figure 22:
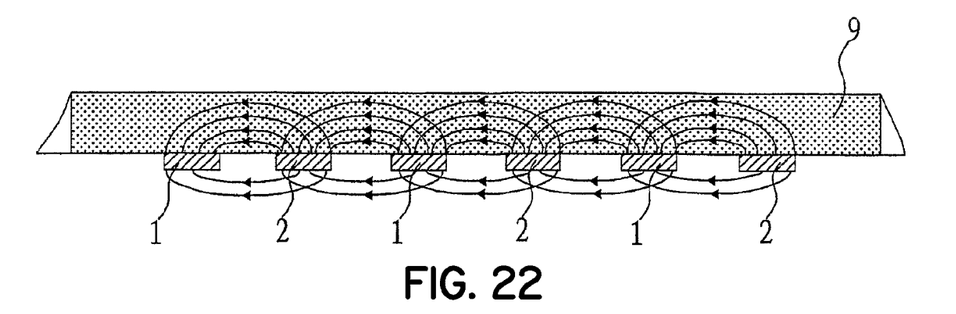
FIG. 22 is a schematic diagram of magnetic field of a plane capacitor composed of round screw planar curve electrodes which is installed on the inner surface of windshield.
Figure 23:
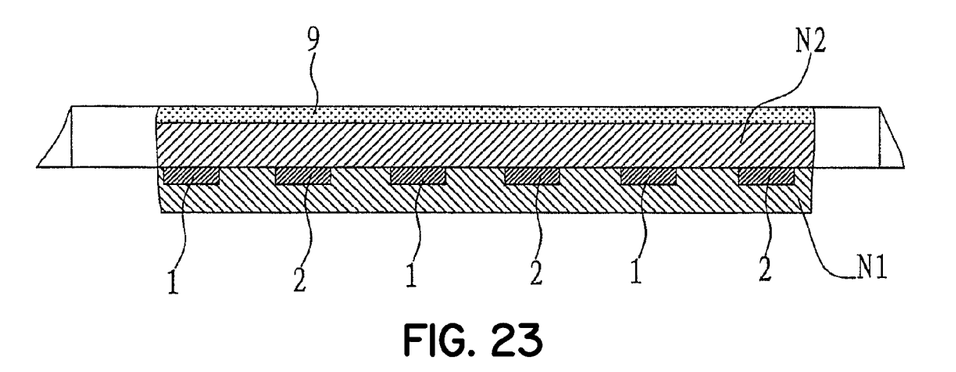
FIG. 23 is a distribution diagram of electric field of a planar curve capacitor under the application environment of present invention.

Referring to FIGS. 15, 22 and 23, there is a slight difference between the capacitance medium space for detecting fog and the medium space for detecting rainwater, the distance d between the two electrodes 1 and 2 of present invention is set far less than the thickness of automobile windshield 9; In this case, the flat medium space around the two electrodes 1 and 2 can be divided into two different spaces: upper flat space N2 placed in the inside of automobile windshield 9 above the planar electrode and lower half flat medium space N1 under the inner surface of automobile windshield and planar curve electrode. As the medium of upper flat space N2 is even glass, dielectric constant and volume of upper flat space N2 can be considered as invariable, and the medium of the lower half space is air; when it is fogging, fine bead will enter space N1, density, size and dielectric constant of the bead will bring the change of effective area, thickness and average dielectric constant of the lower half flat space of N1; in this case, the lower half flat space N1 is exactly our measurement space.

Figure 16:
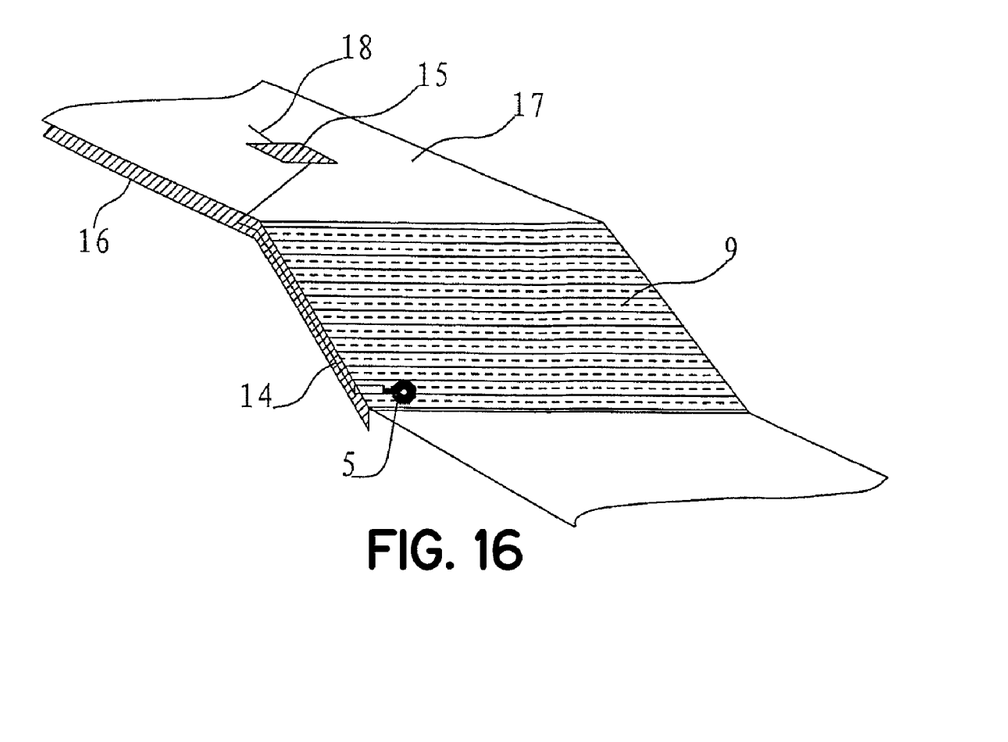
FIG. 16 is a schematic diagram of installation location of a plane capacitor of another embodiment of present invention.

According to the above mentioned principle, referring to FIGS. 15 and 16, present invention can use soft circuit board 5 of transparent plastic film substrate to make a pair of polygonal screw planar curve electrode with radius of r=3 cm, distance of d=0.5 mm and line width of 0.3 mm, the total area of said two electrodes is about 10 cm$^2$, wherein, electrodes 1 and 2 will form two electrodes of the plane capacitor respectively. According to the theory of cross-ventilation between cold and hot air, when cold air goes down, hot air goes up; therefore, generally speaking, fogging of automobile windshield 9 often first starts from the bottom and goes up later. Directed to left handle drive automobiles, said plane capacitor is adhered on lower right corner of the inner surface of automobile windshield 9; directed to right handle drive automobiles, the plane capacitor is adhered on lower left corner of the inner surface of automobile windshield 9; selection of above mentioned positions will not only enable the plane capacitor not influence sight of driver, but also enable it to test fogging degree accurately and timely. The inner surface of automobile windshield 9 is adhered with a curve capacitor produced by planar soft circuit board 5, extended parts of the soft circuit board 5 stretch out into interlayer between roof outer shell 17 and roof inner decoration 16. One end of the two shielded wires 14 will be soldered on two electrodes 1 and 2 of the planar curve capacitor and introduce shielded wires 14 into the interlayer between roof outer shell 17 and roof inner decoration 16; the other end of the two shielded wires 14 is electrically connected with intelligent signal processing unit circuit board 15 installed on the interlayer between roof outer shell 17 and roof inner decoration 16, the circuit board 15 will be electromagnetic shielded and protected by a plastic outer shell with shield, digital output signals of the sensor will be transmitted to the control unit of automatic demisting system through shield LIN bus line cable 18.

Referring to Fig 8, in the above mentioned preferred embodiment of this invention, one electrode of the plane capacitor is connected with output end of the sine-wave generating circuit 31; the other electrode of the plane capacitor is connected with input end of programme-controlled analog signal magnifier and filter circuit 32; the latter accepts programme control from micro processor 34 to conduct range self-adaptive adjustment, sine-wave signal 35 generated by sine-wave generating circuit 31 with a certain frequency will be reduced to sine-wave signal 37 after passing through plane capacitor, the signal 37 will be accepted by programme-controlled analog signal magnifier and filter circuit 32, and generate a DC voltage signal after being magnified and filtered, which will be converted to digital voltage signals via an analog-to-digital conversion circuit 33 and be sent to micro-processor 34, the digital voltage signal will, after being digital filtered, digital linearized processed and digital self-adaptive arithmetic adjusted in micro processor 34, form digital output signals of the sensor and be transmitted to bus line interface circuit 36 of LIN (Local Interconnect Network), then, be delivered to control units of automatic demisting system through shielded LIN bus line cable 18. When the demisting system starts to work, this device continues to detect the surface of windshield and generate feedback signals to further control the demisting system to work and for a close-loop control system, so as to enable the device to control the demisting system to work according to fogging degree.

Figure 17:
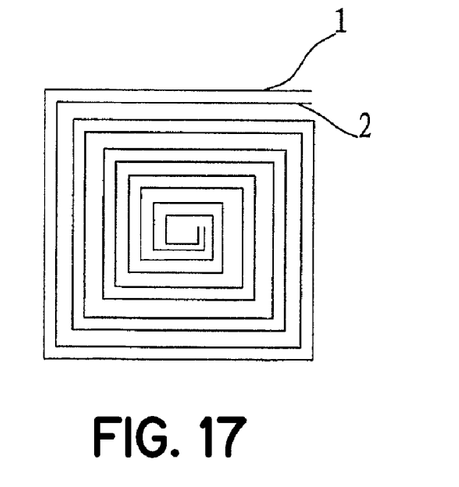
FIG. 17 is a schematic diagram of a plane capacitor composed of rectangle screw planar curve electrodes.
Figure 18:
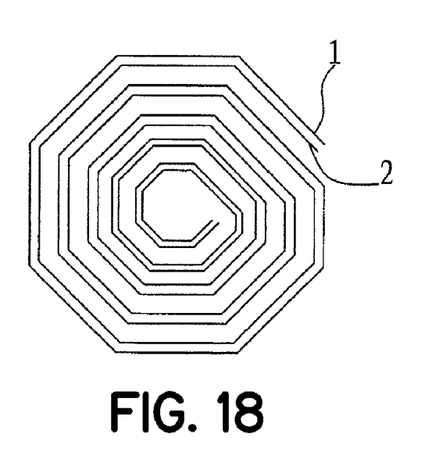
FIG. 18 is a schematic diagram of a plane capacitor composed of polygon screw planar curve electrodes.
Figure 19:
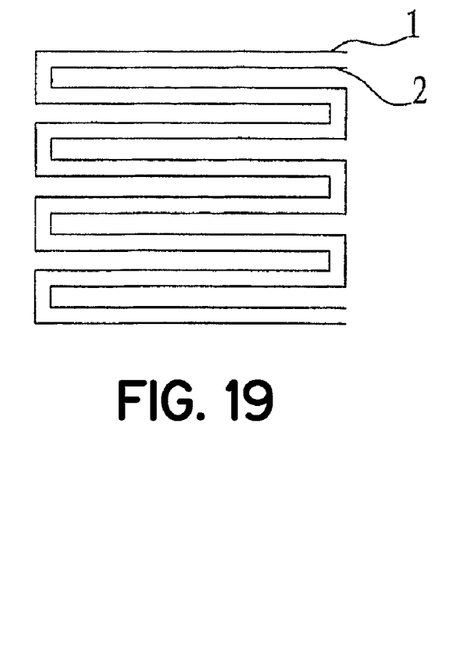
FIG. 19 is a schematic diagram of a plane capacitor composed of rectangle fold line planar curve electrodes.
Figure 20:
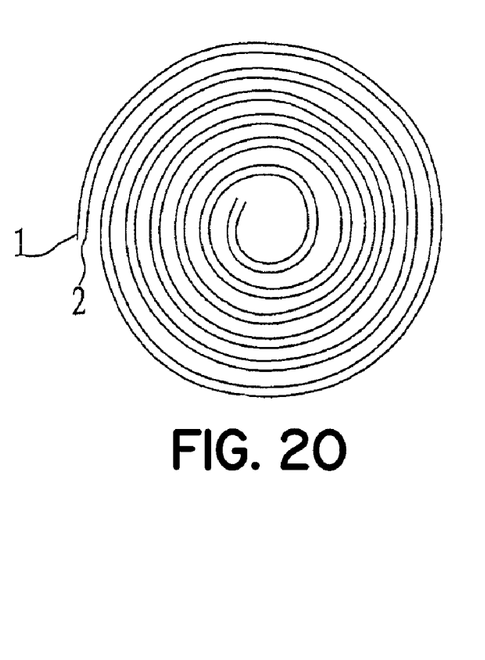
FIG. 20 is a schematic diagram of a plane capacitor composed of round screw planar curve electrodes.
Figure 21:
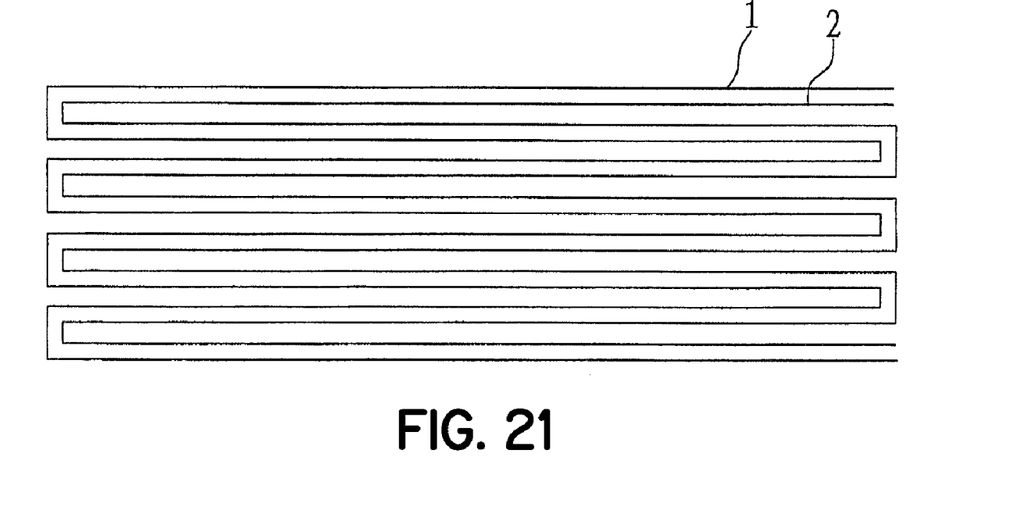
FIG. 21 is a schematic diagram of a plane capacitor composed of rectangle parallel-lined planar curve electrodes.

Various conductive materials can be served as electrode in the automatic demisting sensor provided in present invention, such as: copper, aluminium, silver, conductive rubber, conductive plastics, conductive glue and transparent conductive film. Form a pair of planar curve electrodes on a position above the inner surface of automobile windshield not influencing sight of driver through various technology methods, such as: bonding, compression jointing and spraying; the planar electrode can be in various shapes, among which, FIG. 17 shows a rectangular screw plane capacitor, FIG. 18 shows a polygonal screw plane capacitor, FIG. 19 shows a rectangular fold line plane capacitor. F FIG. 20 shows a round screw plane capacitor and FIG. 21 shows a rectangular parallel line plane capacitor. It is required that the planar curve electrode should be closely contacted with the inner surface of windshield, and plating metal on windshield surface will be the best choice.

Experiments show that a distance of 0.5 mm between planar curve electrodes is appropriate, and appropriate width of curve electrode is less than 0.3 mm. Any bonding means including jointing, compression jointing, bonding or conductive rubber to introduce the two electrodes by leads and the best lead to introduce is shielded line.

Below is the method for detecting environmental change of automobile windshield surface by the above mentioned device:

Referring to FIG. 26, according to the detecting methods provided by present invention, it includes the following steps: a. Initialize detecting device; b. The signal generator 31 of the detecting device generates a testing signal 35 which will be transmitted to the plane capacitor; c. Measure value variations of the testing signal 35; d. Transmit the testing signal 35 to the processing unit; e. The processing unit generates control signals according to variations of the testing signal 35; f. Transmit control signals to the equipment; g. Detecting device re-measure windshield surface, generate feedback signals, transmit to the processing unit and form a close-loop control system.

The initialization of the detecting device in present invention is to test and set static initial value of the sense element of the plane capacitor according to materials and thickness of automobile windshield, area and installation means of the sense element of plane capacitor, environmental temperature and humidity conditions; as different substance has different dielectric constants, the detecting device can set different initial values according to different substances so as to judge which kind of substance is attached to the glass surface. For instance, when water is attached to the glass surface formed by a plane capacitor, capacitance value of the plane capacitor will change accordingly, and the establishment of variation of the capacitor in this case will be served as a standard for judging water attachment on glass surface.

The frequency of said testing signal in present invention is 100 kHz~1000 kHz. Using the above mentioned frequency can satisfy measurement requirements of this invention, and enhance measurement accuracy of this invention. Static initial value of said plane capacitor is between 0.2–5 pf, which can make the planar capacitor have a higher sensitivity and satisfy the requirements of present invention.

Referring to FIGS. 5, 8 and 26, the methods of this invention is realized in this way: a plane capacitor is set on the inner surface of automobile windshield 9, the two electrodes 1 and 2 of said plane capacitor will be placed on same plane, serving as sensing elements to measure environmental change of windshield 9; variable signals of capacitance Cx brought by outer environment influence to said plane capacitor will be transmitted to sensor detecting circuit 3, and said sensor detecting circuit 3 will generate control signals controlling equipment work according to variations in capacitance Cx tested. The said sensor detecting circuit 3 include a signal generator 31, a programme-controlled analog signal magnifier and filter circuit 32, an analog-to-digital conversion circuit 33, micro-processor 34, said signal generator 31 generates a testing signal 35 accessing to the plane capacitor, the variations of the testing signal 35 can reflect variations of capacitance Cx in said plane capacitor, consequently, variations of the testing signal 35 can reflect environmental change on windshield surface. The testing signal 35 of said plane capacitor will, after being entered into programme-controlled analog signal magnifier and filter circuit 32 and magnified and filtered, generate a DC voltage signal, the said DC voltage signal will convert to digital voltage signal after passing through said analog-to-digital conversion circuit 33, said micro-process 34 will accept said digital voltage signals and conduct digital filter, linearized digital processing and digital self-adaptive arithmetic adjustment to said digital voltage signals so as to form digital output signals of the sensor to control equipment work. Said equipments can either be wiper device or demisting device.

The invention claimed is:

1. A device for detecting environmental change of an automobile windshield, comprising:
    a plane capacitor including two electrodes disposed on a common plane on an inner surface of said windshield, the electrodes having a total area of less than 100 cm$^2$, environmental change of said windshield effecting a change in capacitance of the plane capacitor; and
    a sensor circuit operatively coupled with the plane capacitor and adapted to couple test signals to the plane capacitor and receive said test signals therefrom modified in relation to said change in capacitance so as to develop change signals corresponding to environmental change of said windshield, such that equipment working on said windshield in response to the change signals operates in closed-loop fashion to affect said environmental change of said windshield;
    said sensor circuit including a signal generator adapted to generate said test signals, a programme-controlled analog signal magnifier and filter circuit adapted to receive the test signals as modified and output DC voltage signals in relation thereto, an analog-to-digital conversion circuit to convert the DC voltage signals to digital signals, and a micro-processor adapted to digitally process the digital signals and output change signals for control of said equipment.

2. The device of claim 1, the electrodes having a shape selected from the group consisting of rectangle, fan-shaped, triangle, polygon, fold line, screw line and parallel line.

3. The device of claim 1, the plane capacitor including two staggered pectinate electrodes.

4. The device of claim 3, the two electrodes being spaced apart a distance less than a thickness of said windshield thereat.

5. The device of claim 3, the line width of the two electrodes being less than 0.3 mm.

6. The device of claim 1, the plane capacitor including parallel wires according to a spacing in curve shape.

7. The device of claim 1, the electrodes being of conductive materials selected from the group consisting of copper, aluminium, silver, conductive rubber chip, conductive plastic, transparent conductive film and conductive rubber.

8. The device of claim 1 wherein each of the electrodes includes a plurality of electrically coupled electrode elements.

9. The device of claim 8 further comprising, for each electrode, leads electrically coupling the electrode elements thereof.

10. The device of claim 1, the plane capacitor being disposed on said windshield inner surface by bonding, compression jointing or spray.

11. The device of claim 1, the sensor circuit adapted to output test signals selected from the group of sine wave, square wave and triangle wave.

12. The device of claim 1, the total area of the electrodes being between 10 to 20 cm$^2$.

13. The device of claim 1, the two electrodes being spaced apart a distance equal to a thickness of said windshield thereat.

14. A method for detecting environmental change of an automobile windshield wherein a plane capacitor including two electrodes disposed on a common plane are on an inner surface of the windshield, the electrodes having a total area of less than 100 cm$^2$, environmental change of said windshield effecting a change in capacitance of the plane capacitor, the method comprising the steps of:
    (a) coupling test signals to the plane capacitor;
    (b) receiving test signals from the plane capacitor modified in relation to said change in capacitance;
    (c) outputting DC voltage signals in relation to the received test signals;
    (d) converting the DC voltage signals to digital signals;
    (e) digitally processing the digital signals to develop change signals corresponding to environmental change of the windshield;
    (f) transmitting the change signals to equipment working on the windshield whereby to affect said environmental change of the windshield; and
    (g) repeating steps (a) through (f) whereby to operate in closed-loop fashion.

15. The method of claim 14 further comprising detecting and setting static initial values according to characteristics of the automobile windshield, characteristics of the plane capacitor, environmental temperature and humidity conditions.

16. The method of claim 14 wherein generating test signals includes generating test signals selected from the group consisting of sine wave, square wave and triangle wave.

17. The method of claim 14 wherein the frequency of the test signal is between about 100 kHz and about 1000 kHz.

18. The method of claim 14, the plane capacitor having a static capacitance between about 0.2 and about 5pf.

19. The method of claim 14 wherein: the equipment is selected from the group consisting of a rain wiper device, a demisting device and a combination thereof.

* * * * *

UNITED STATES PATENT AND TRADEMARK OFFICE
CERTIFICATE OF CORRECTION

| | |
|---|---|
| PATENT NO. | : 7,208,962 B2 |
| APPLICATION NO. | : 10/595085 |
| DATED | : April 24, 2007 |
| INVENTOR(S) | : Tengchen Sun et al. |

It is certified that error appears in the above-identified patent and that said Letters Patent is hereby corrected as shown below:

Column 3
Line 13, "which caused" should be -- caused --.
Line 25, "sensor required" should be -- sensor requires --.
Lines 31-32, "…are used in the prior art." should be -- used in the prior art. --.

Column 4
Lines 32-35, "which will no doubt limits applicable scope of this sensor, Because the windshields applied in automobile industry is available in both double layers and single layer at present." should be -- which no doubt limits applicable scope of this sensor. --.
Line 48, "disturb" should be -- disturbed --.
Lines 66-67, "environmental" should be -- environment --.

Column 5
Line 30, "as long as it wills not influence" should be -- as long as it will not influence --.
Line 44, "sensor cannot detect variations" should be -- sensor's inability to detect variations --.

Column 7
Line 42, "of the medium relatives to vacuum" should be -- of the medium relative to vacuum --.

Column 8
Line 3, "In the FIGS. 10" should be -- In FIG. 10 --.
Lines 24-25, "…in direct ration with … and in inverse ration with…" should be -- …in direct ratio with … and in inverse ratio with… --.
Line 30, "the bottom of glass 9, We" should be -- the bottom of glass 9. We --.
Line 51, "invention. Among which, The parallel" should be --invention, among which the parallel --.

Column 9
Line 30, "and behind of the automobile" should be -- and behind the automobile --.

UNITED STATES PATENT AND TRADEMARK OFFICE
CERTIFICATE OF CORRECTION

PATENT NO. : 7,208,962 B2
APPLICATION NO. : 10/595085
DATED : April 24, 2007
INVENTOR(S) : Tengchen Sun et al.

It is certified that error appears in the above-identified patent and that said Letters Patent is hereby corrected as shown below:

Column 10
Line 10, "Lcal" should be -- Local --.
Line 20, "FIG. 4, 11 to 14," should be -- FIGS. 4, 11 to 14, --.
Line 64, "in present invention; the below is" should be -- in the present invention, below is --.

Column 11
Lines 36-37, "enable the plane capacitor not influence" should be -- enable the plane capacitor to not influence --.

Column 12
Line 24, "F FIG. 20" should be -- FIG. 20 --.
Line 38, "Referring to FIG. 26, according to" should be -- According to --.

Column 13
Lines 3-4, "FIGS. 5, 8, and 26, the methods of this invention is realized" should be -- FIGS. 5 and 8, the methods of this invention are realized --.
Line 13, "circuit 3 include a" should be -- circuit 3 includes a--.
Line 25, "micro-process" should be -- micro-processor --.

Claim 14
Column 14, Line 28, "plane are on" should be -- plane on --.

Signed and Sealed this

Twenty-seventh Day of May, 2008

JON W. DUDAS
*Director of the United States Patent and Trademark Office*